United States Patent
Bracken et al.

(10) Patent No.: US 11,389,134 B2
(45) Date of Patent: Jul. 19, 2022

(54) SYSTEM AND METHOD TO FIND IMPROVED VIEWS IN TRANSCATHETER VALVE REPLACEMENT WITH COMBINED OPTICAL SHAPE SENSING AND ULTRASOUND IMAGE GUIDANCE

(71) Applicant: KONINKLIJKE PHILIPS N.V., Eindhoven (NL)

(72) Inventors: John Allan Bracken, Denver, CO (US); Bharat Ramachandran, Morganville, NJ (US); Molly Lara Flexman, Melrose, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 833 days.

(21) Appl. No.: 15/755,747

(22) PCT Filed: Sep. 13, 2016

(86) PCT No.: PCT/IB2016/055432
§ 371 (c)(1),
(2) Date: Feb. 27, 2018

(87) PCT Pub. No.: WO2017/051279
PCT Pub. Date: Mar. 30, 2017

(65) Prior Publication Data
US 2018/0256131 A1    Sep. 13, 2018

Related U.S. Application Data

(60) Provisional application No. 62/232,049, filed on Sep. 24, 2015.

(51) Int. Cl.
*A61B 8/12* (2006.01)
*A61B 8/08* (2006.01)
(Continued)

(52) U.S. Cl.
CPC .............. *A61B 8/12* (2013.01); *A61B 8/0883* (2013.01); *A61B 8/4416* (2013.01); *A61B 8/467* (2013.01);
(Continued)

(58) Field of Classification Search
None
See application file for complete search history.

(56) References Cited

U.S. PATENT DOCUMENTS

| | | | |
|---|---|---|---|
| 2010/0240996 A1* | 9/2010 | Ionasec | G06T 7/262 600/443 |
| 2011/0222750 A1* | 9/2011 | Liao | A61B 6/503 382/131 |

(Continued)

FOREIGN PATENT DOCUMENTS

| | | |
|---|---|---|
| JP | 2004049558 A | 2/2004 |
| WO | 2015071343 A1 | 5/2015 |

OTHER PUBLICATIONS

University of Minnesota. "Cardiac Valve Nomenclature". Atlas of Human Cardiac Anatomy. Regents of the University of Minnesota, 2020. (Year: 2020).*
(Continued)

*Primary Examiner* — Yi-Shan Yang

(57) ABSTRACT

A system for finding improved views includes a shape sensing optical fiber system disposed on or in a prosthesis to track the prosthesis in a volume. A real-time imaging system employs a non-ionizing radiation source to image the volume having the prosthesis and reference positions in the volume. A search program is stored in memory to search images of the real-time imaging system to identify the reference positions in the volume. An image processing device overlays shape sensing data and images from the real-time imaging system and computes an improved view in accordance with improved view parameters.

15 Claims, 6 Drawing Sheets

(51) Int. Cl.
*A61B 8/00* (2006.01)
*A61B 34/20* (2016.01)
*A61B 34/00* (2016.01)

(52) U.S. Cl.
CPC ............ *A61B 8/485* (2013.01); *A61B 8/5261* (2013.01); *A61B 34/20* (2016.02); *A61B 34/25* (2016.02); *A61B 8/463* (2013.01); *A61B 2034/2061* (2016.02); *A61B 2034/2065* (2016.02); *A61B 2034/252* (2016.02)

(56) References Cited

U.S. PATENT DOCUMENTS

| | | | | |
|---|---|---|---|---|
| 2012/0065498 | A1* | 3/2012 | Redel | A61B 8/0883 600/424 |
| 2012/0232386 | A1* | 9/2012 | Mansi | A61B 8/5238 600/437 |
| 2013/0071001 | A1* | 3/2013 | Waechter-Stehle | A61B 90/39 382/132 |
| 2014/0052241 | A1* | 2/2014 | Harks | A61B 34/20 623/2.11 |
| 2014/0330133 | A1* | 11/2014 | Stern | A61B 5/6853 600/479 |
| 2015/0223773 | A1* | 8/2015 | John | A61B 6/503 600/424 |
| 2015/0282890 | A1* | 10/2015 | Cohen | A61B 6/487 600/424 |
| 2015/0282931 | A1* | 10/2015 | Brunnett | A61F 2/2418 623/2.11 |
| 2016/0354057 | A1* | 12/2016 | Hansen | A61B 8/483 |
| 2018/0014889 | A1* | 1/2018 | Denissen | A61B 34/20 |

OTHER PUBLICATIONS

Cilingiroglu et al. "Step-by-Step Guide for Percutaneous Mitral Leaflet Repair". Cardiac Interventions Today. Jul./Aug. 2010 (Year: 2010).*

* cited by examiner

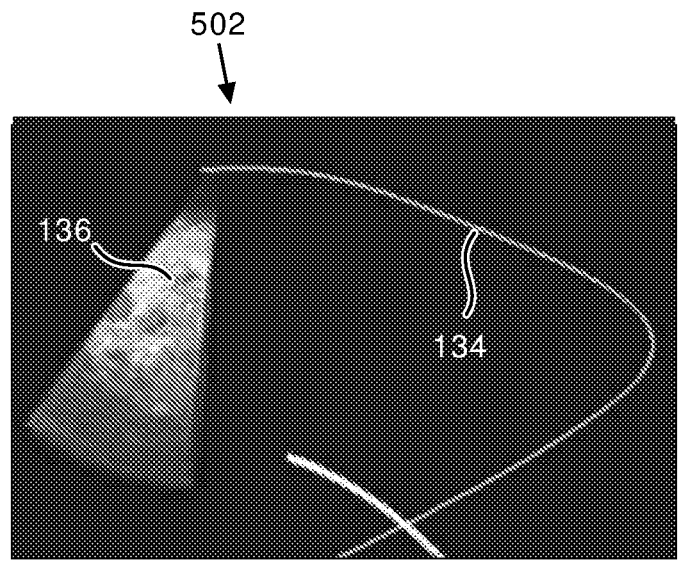
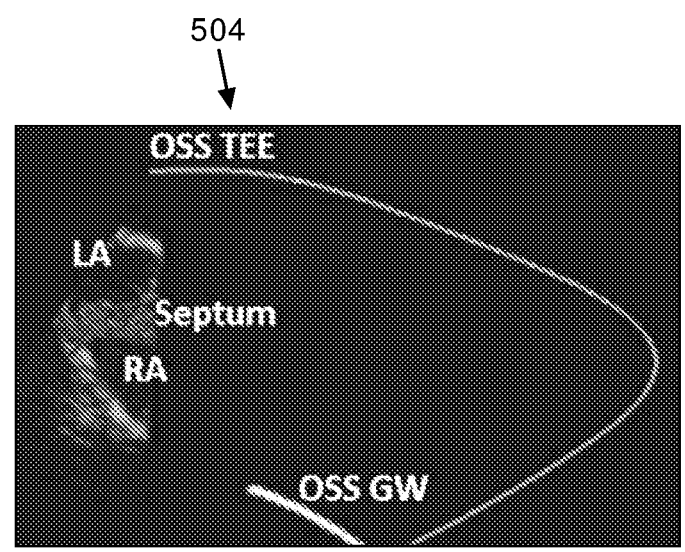
FIG. 5

SYSTEM AND METHOD TO FIND IMPROVED VIEWS IN TRANSCATHETER VALVE REPLACEMENT WITH COMBINED OPTICAL SHAPE SENSING AND ULTRASOUND IMAGE GUIDANCE

CROSS-REFERENCE TO PRIOR APPLICATIONS

This application is the U.S. National Phase application under 35 U.S.C. § 371 of International Application Serial No. PCT/IB2016/055432, filed on Sep. 13, 2016, which claims the benefit of U.S. Patent Application No. 62/232,049, filed on Sep. 24, 2015. This application is hereby incorporated by reference herein.

BACKGROUND

Technical Field

This disclosure relates to medical instruments and more particularly to medical imaging and guidance using shape sensing optical fibers and ultrasound for valve replacement.

Description of the Related Art

Shape sensing with optical fibers uses light along a multicore or collection of single core optical fiber for device localization and navigation during surgical intervention. One principle involved makes use of distributed strain measurement in the optical fiber using characteristic Rayleigh backscatter or controlled grating patterns. The shape along the optical fiber begins at a specific point along the sensor, known as the launch point (or z=0), and the subsequent shape position and orientation are relative to that point. For meaningful clinical use, shape-sensed devices can be registered to an imaging frame of reference (such as a preoperative computed tomography (CT) or a live fluoroscopy image).

During transcatheter aortic valve replacement (TAVR) procedures in a catheter lab or hybrid operating room, a key required task is determining an improved imaging view to help guide the deployment of a prosthetic valve in the aortic annulus. This view depends on a number of factors including patient anatomy, the specific bioprosthetic valve being deployed, and the patient positioning. As more devices enter the market, different improved views for each of them may be required. The improved view is found using either 2D live x-ray aortography and live x-ray fluoroscopy, computed tomography (CT) or C-arm computed tomography (C-arm CT). When live x-ray imaging is used to guide TAVR procedures, a specific angle and orientation for the x-ray C-arm will provide the improved view for deployment. All of these imaging approaches to find an improved view require the patient to be exposed to ionizing radiation and nephrotoxic contrast agent.

SUMMARY

In accordance with the present principles, a system for finding improved views includes a shape sensing optical fiber system disposed on or in a prosthesis to track the prosthesis in a volume. A real-time imaging system employs a non-ionizing radiation source to image the volume having the prosthesis and reference positions in the volume. A search program is stored in memory to search images of the real-time imaging system to identify the reference positions in the volume. An image processing device overlays shape sensing data and images from the real-time imaging system and computes an improved view in accordance with selected improved view parameters.

Another system for finding improved views includes a shape sensing optical fiber system disposed on or in a prosthesis to track the prosthesis in a volume. The shape sensing optical fiber system generates shape data indicating a location and position of the prosthesis within the volume. An ultrasonic imaging system creates real-time anatomical images of the volume having the prosthesis and the volume. A registration module is configured to register the shape data with the real-time images. A search program is stored in memory to search the real-time images to identify reference positions in the volume. An image processing device overlays the registered shape data and the real-time images and compute an improved view in accordance with selected improved view parameters. A processor unit configures the ultrasonic imaging system to maintain the improved view.

A method for finding improved views includes tracking a prosthesis in a volume using a shape sensing optical fiber system to generate shape data; real-time imaging with a non-ionizing radiation source to image the volume having the prosthesis in the volume; searching the real-time images to identify reference positions in the volume; processing the real-time images and the shape data to overlay the real-time images and the shape data; computing an improved view in accordance with improved view parameters; and obtaining the improved view for positioning the prosthesis.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein:

FIG. 5 is an ultrasound cardiac image derived from a full volume based on geometric information from features in ultrasound or positioning of the device (shape sensing) in accordance with one embodiment;

DETAILED DESCRIPTION OF EMBODIMENTS

Figure 1:
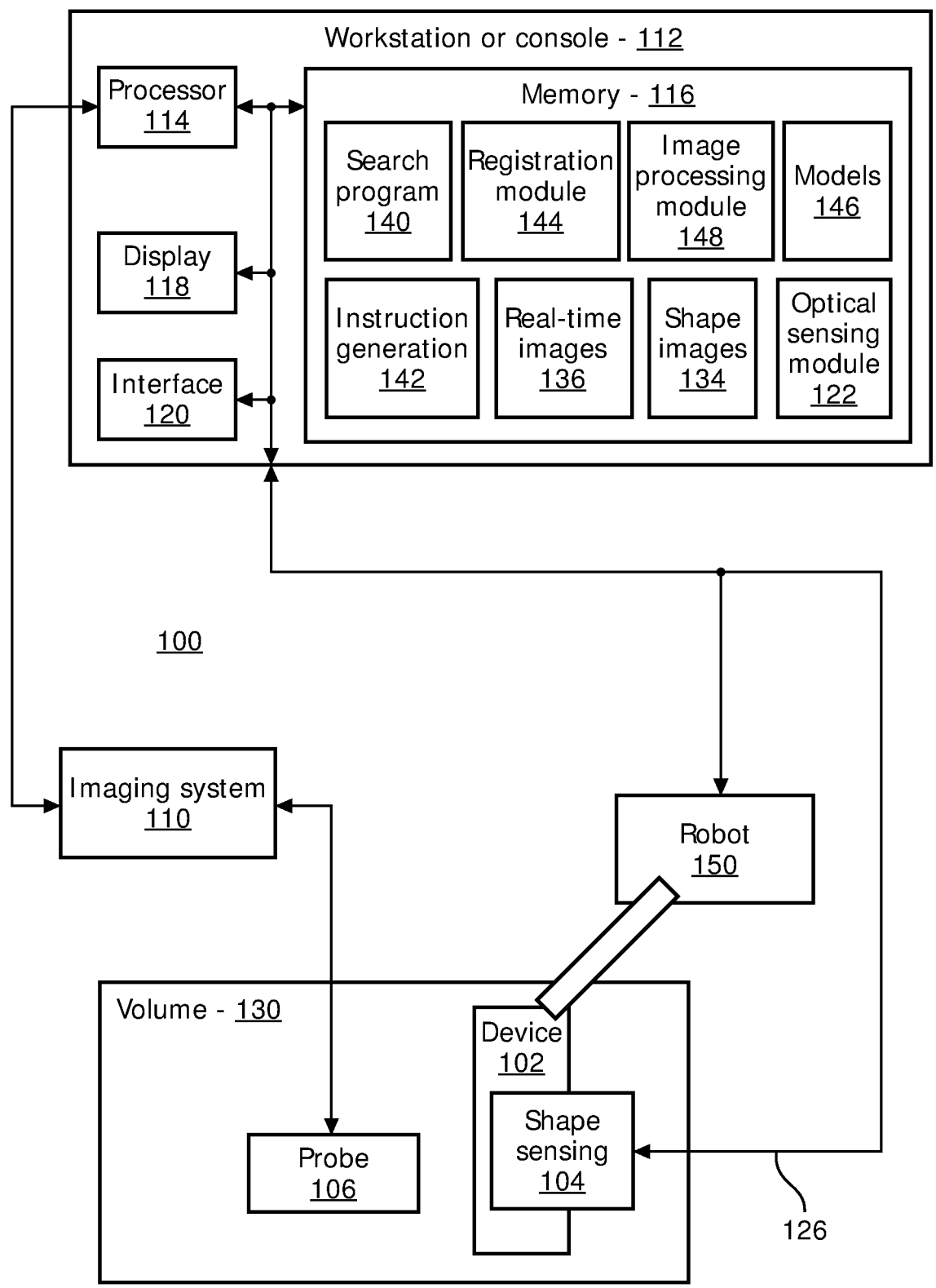
FIG. 1 is a block/flow diagram showing a system for finding improved views using shape sensing enabled devices with real-time imaging in accordance with one embodiment.

In accordance with the present principles, systems and methods are provided for finding improved imaging views to deploy medical devices, such as a bioprosthetic valve for a transcatheter aortic valve replacement (TAVR) procedure. In one embodiment, the improved view shows an aortic annulus in a favorable orientation to deploy the bioprosthetic valve safely and effectively. This view conventionally may be obtained using x-ray aortography, x-ray fluoroscopy (live x-ray), computed tomography (CT), C-arm computed tomography (C-arm CT), etc. However, all of these imaging modalities use ionizing radiation exposure and contrast agent, which introduce additional risks to the patient.

In useful embodiments, methods are provided in which Fiber-Optic Real Shape™ (FORS™, also known as "Optical Shape Sensing", "Fiber Shape Sensing", "Fiber Optical 3D Shape Sensing", "Fiber Optic Shape Sensing and Localization" or the like) may be combined with ultrasound imaging (e.g., transthoracic or transesophageal echocardiography) to determine an improved view for prosthetic valve deployment in TAVR procedures. These methods employ FORS™ information of the bioprosthetic valve to generate an outline of the device, combined and overlaid with live ultrasound imaging (or other imaging modalities). Cusp nadirs of the native valve are automatically detected in the ultrasound image sequence (or other imaging modality), along with the geometric device information from FORS™ This information is then sent to the FORS™ and ultrasound systems as feedback to update the ultrasound view to display the nadirs in an improved view configuration, along with instructions to the user or a robotic system as to how to orient the device properly in the improved view before deployment. This can be used to mitigate the amount of x-ray image guidance currently needed to find the view and to deploy the bioprosthetic valve.

Fiber-Optic Real Shape™ system is a commercial name for systems developed by Koninklijke Philips, N.V. As used herein, the terms FORS™ and FORS™ systems are not, however, limited to products and systems of Koninklijke Philips, N.V., but refer generally to fiber optic shape sensing and fiber optic(al) shape sensing systems, fiber optic 3D shape sensing, fiber optic 3D shape sensing systems, fiber optic shape sensing and localization and similar technologies. FORS™ systems are also commonly known as "optical shape sensing systems"

It also should be understood that the present invention will be described in terms of medical instruments; however, the teachings of the present invention are much broader and are applicable to any systems that employ fiber optic shape sensing registered to other imaging modalities. In some embodiments, the present principles are employed in tracking or analyzing complex biological or mechanical systems. In particular, the present principles are applicable to internal tracking procedures of biological systems and procedures in all areas of the body such as the lungs, gastro-intestinal tract, heart, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, a system 100 for finding improved views using shape sensing enabled devices with real-time imaging (e.g., ultrasound) is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store an optical sensing module 122 configured to interpret optical feedback signals from a shape sensing device or system 104. Optical sensing module 122 is configured to use the optical signal feedback (and any other feedback) to reconstruct deformations, deflections and other changes associated with a medical device or instrument 102 and/or its surrounding region. The medical device 102 may include a catheter, a guidewire, a probe, an endoscope, a robot, an electrode, a filter device, a balloon device, or other medical component, etc. In a useful embodiment, the medical device 102 includes an implantable device, and more specifically a prosthetic heart valve. The medical device 102 is coupled with a shape sensing system, such as e.g., FORS™ system.

The system 104 on device 102 includes one or more optical fibers 126 which are coupled to the device 102 in a set pattern or patterns. The optical fibers 126 connect to the workstation 112 and provide data to the optical sensing module 122 to generate shape images 134 of the device 102 and stored in memory 116.

System 104 with fiber optics may be based on fiber optic Bragg grating sensors, Rayleigh scattering, or other types of scattering. Inherent backscatter in conventional optical fiber can be exploited, such as Raleigh, Raman, Brillouin or fluorescence scattering. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

A fiber optic Bragg grating (FBG) system may also be employed for system 104. FBG is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

Fresnel reflection at each of the interfaces where the refractive index is changing is measured. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors.

Incorporating three or more cores or three or more single-core fibers permits a three dimensional form of such a structure to be precisely determined. From the strain measurement, the curvature of the structure can be inferred at that position. From the multitude of measured positions, the total three-dimensional form is determined.

System 100 includes a real-time imaging system 110 to image a volume 130 during a procedure. Imaging system 110 preferably employs non-ionizing radiation for imaging the volume 130. In one embodiment, the imaging system 110 includes an ultrasound system, which employs a probe 106. The probe 106 may be employed internally or externally with respect to the volume 130. Real-time images 136 (although preoperative images may be employed as well instead of or in addition to the real-time images) are stored in memory 116.

In one embodiment, workstation 112 includes an image processing module 148 configured to receive and display feedback from the system 104 and system 110 on a display 118. System 104 and system 110 provide two perspectives to permit positioning of a prosthetic device 102 within the volume 130. A registration module 144 employs alignment points from the device 102 (as determined by images 134 from shape sensing by system 104) and aligns these points with the information generated in the real-time images 136 (from system 110).

Workstation 112 includes the display 118 for viewing internal images of a subject (patient) or volume 130 and may include the images 134 and 136 as overlays or other renderings. The image processing module or device 148 overlays shape sensing data and images from the real-time imaging system 110 to provide a combined image. The image processing module 148 along with the processor 114 computes an improved view in accordance with selected improved view parameters for display on the display 118. The display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

In one embodiment, the system 100 may be employed in transcatheter aortic valve replacement (TAVR) procedures. The system 100 combines and overlays FORS™ technology with live ultrasound imaging (e.g., transthoracic echocardiography (TTE), transesophageal echocardiography (TEE), etc. The system 100 determines an improved view for bioprosthetic valve deployment in TAVR procedures. These two modalities provided by systems 104 and 110 combine to display all the relevant aortic anatomy overlaid with the outline (imaged or modeled) of the prosthetic valve shape (device 102), in real-time and in three dimensions, without the use of ionizing radiation or contrast agent. The aortic annulus and all three valve cusps would also be shown in real-time, providing additional functional information of these structures. The improved view could also be updated in real-time due to the live aspects of both of these modalities.

Using the ultrasound TEE and/or TTE imaging system 110, an automatic search program 140 conducts a search of the images 136 around a region of the native aortic annulus to locate the positions of all three cusp nadirs in three dimensional space. The cusp nadirs will then be automatically marked and labeled in the ultrasound images using the image processing module 148. Concurrently, the device 102 (e.g., bioprosthetic valve) will be optically shape sensed using system 104, so its 3D position and orientation will be tracked in real-time. The combined image guidance approach using images 134 and 136 provides both the geometric information of the cusp nadirs in the ultrasound images 136 and the geometric information/images 134 of the shaped-sensed bioprosthetic valve 102.

Based on a pre-determined set of parameters for an improved view (e.g., spatial relationships between anatomical and/or prosthesis reference positions), a transform or other model 146 may be employed to determine movements needed to position the improved view from a current view. This may include determining how to redirect an ultrasonic beam or determine a position of the ultrasonic probe, etc. An instruction generator 142 may be programmed to convert the position transition movements from the current view to the improved view to verbal (speech or text) instructions to a user or to machine language or other code to guide a robot or automated robotic platform 150. The robot 150 may position the device or imaging probe 106 or both.

The pre-determined set of parameters may include, e.g., an aortic slice plane, cusp nadir alignment and relative distance and position in the images 136, etc. In one embodiment, the processor 114 or instruction generator 142 sends the instructions to the ultrasound imaging system 110 to select an image slice (or slices) needed to display the improved view.

Feedback regarding the device 102 may also be sent to the image processing module 148, enabling the display of instructions to an interventionalist as to how to properly orient the device 102 in the improved view, or to send these instructions to the automated robotic platform 150, which can then orient the device 102 and/or probe 106 correctly in the improved view prior to deployment.

The image processing module 148 can also generate perspective views or views from different positions in the volume 130. In one embodiment, the image processing module 148 can switch between improved views including a view for a delivery device, e.g., a guide wire or catheter (not shown) for delivering the prosthesis/device 102, a view for a native valve in the volume 130, a view for another anatomy of interest, etc. The display 118 may display images switched between the improved view(s) for the native aortic or mitral valve and the improved view for the device (102) visualization. A simultaneous display may be rendered of the native valve improved view and the device improved view (side by side). Other imaging perspectives and display rendering configurations are also contemplated.

In one embodiment, the prosthesis/device 102 or the model 146 of the prosthesis 102 may be rendered in the display 118. This provides a visualization of the position and orientation of the prosthesis or a representation (146) of the prosthesis 102 to provide a surgeon with the proper information for carrying out the procedure.

Figure 2:
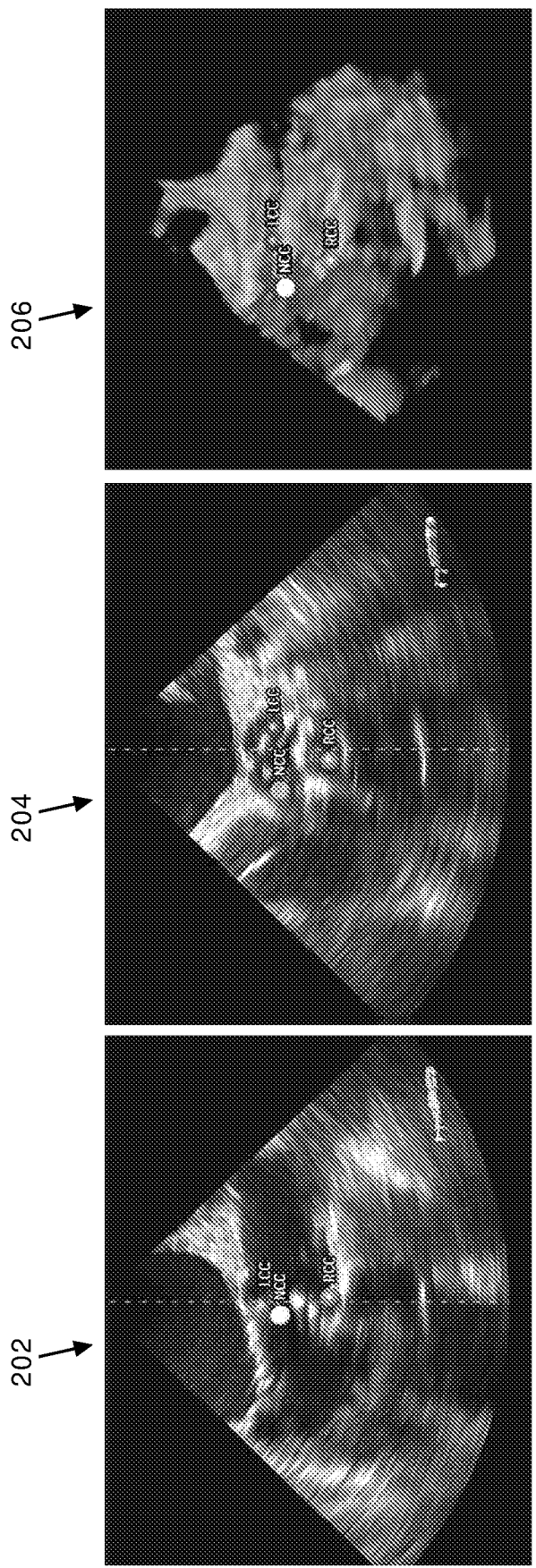
FIGS. 2A and 2B are two-dimensional echocardiography (ultrasound) images showing nadir cusps identified in accordance with one embodiment.
FIG. 2C is a three-dimensional echocardiography (ultrasound) image showing nadir cusps identified in accordance with one embodiment.

Referring to FIGS. 2A, 2B and 2C, a left coronary cusp (LCC), right coronary cusp (RCC) and non-coronary cusp (NCC) of the native aortic valve are marked on 2D echocardiography images 202, 204 in FIGS. 2A and 2B. The long axis image is shown in image 202, and the short axis view is shown in image 204. FIGS. 2A and 2B show locations and markings of the native aortic valve cusp nadirs from 2D (showing short and long axis view). FIG. 2C shows a 3D echocardiography image 206 showing the marked cusps. FIG. 2C shows locations and markings of the native aortic valve cusp nadirs from 3D echocardiography image sequences.

Referring again to FIG. 1, the native valve cusp nadirs may be located automatically using the search program 140. Sent as an instruction from the processor 114 to the image processing module 148 or ultrasound imaging system 110, the search program 140 locates the three cusp nadirs in the images 136 generated by the ultrasound system 110 and then automatically marks the nadirs (e.g., LCC, RCC, NCC in FIGS. 2A, 2B and 2C). This search program 140 may be based on previously acquired 3D ultrasound models of the aortic structure around the aortic root. These models would assist to provide as an initialization point to begin the search for the cusp nadirs. The search program 140 may search using groups of pixels, boundaries, or other image information to locate and mark the nadirs in the anatomical images.

With FORS™, it is possible to generate a real-time outline in three dimensions of the device 102 (e.g., the bioprosthetic valve) and its delivery system. FORS™ is able to track the geometric position and orientation of the prosthetic valve device 102 in real-time. With image registration performed by a registration module 144, the ultrasound image sequence images 136 can be overlaid with the shape-sensed device data/images 134. Registration by the registration module 144 may be performed using known methods to align coordinate systems of the imaging modalities (e.g., for systems 104 and 110).

Figure 3:
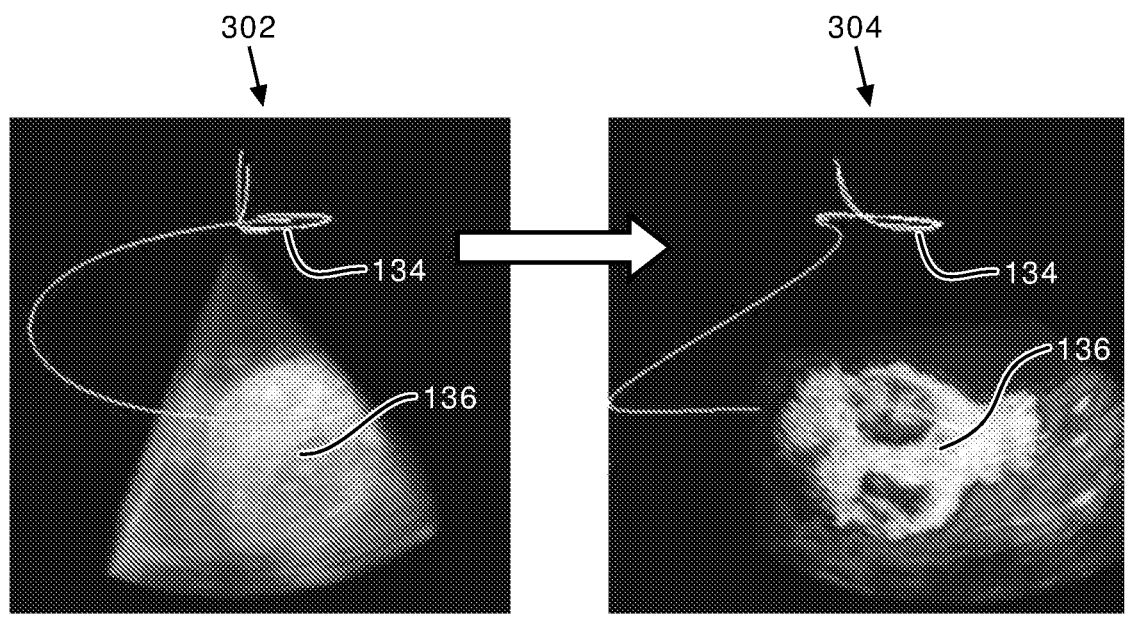
FIG. 3 shows registered overlay images depicting an ultrasound image and an optical shape sensing image in accordance with one embodiment.

Referring to FIG. 3, registered overlay images 302, 304 are illustratively shown depicting an ultrasound image 136 and an optical shape sensing image 134. A selection of an improved 2-chambered view in image 304 is based on the position of the device 102 from the volume on the image 302.

Once the search program 140 (FIG. 1) locates and labels the native valve cusp nadirs, this geometric information can be sent back to the processor 114, which will then calculate and optimize the ultrasound beam orientation needed to generate the improved view. The ultrasound beam configuration will be selected by the processor 114 based on a desired improved view for a specific device. For the Edwards™ SAPIEN™ valve, the ultrasound beams will be configured such that the cusp nadirs are displayed in a view that shows them on a common line with each other and equidistant from each other (e.g., the improved view parameters), as depicted in FIG. 4.

Figure 4:
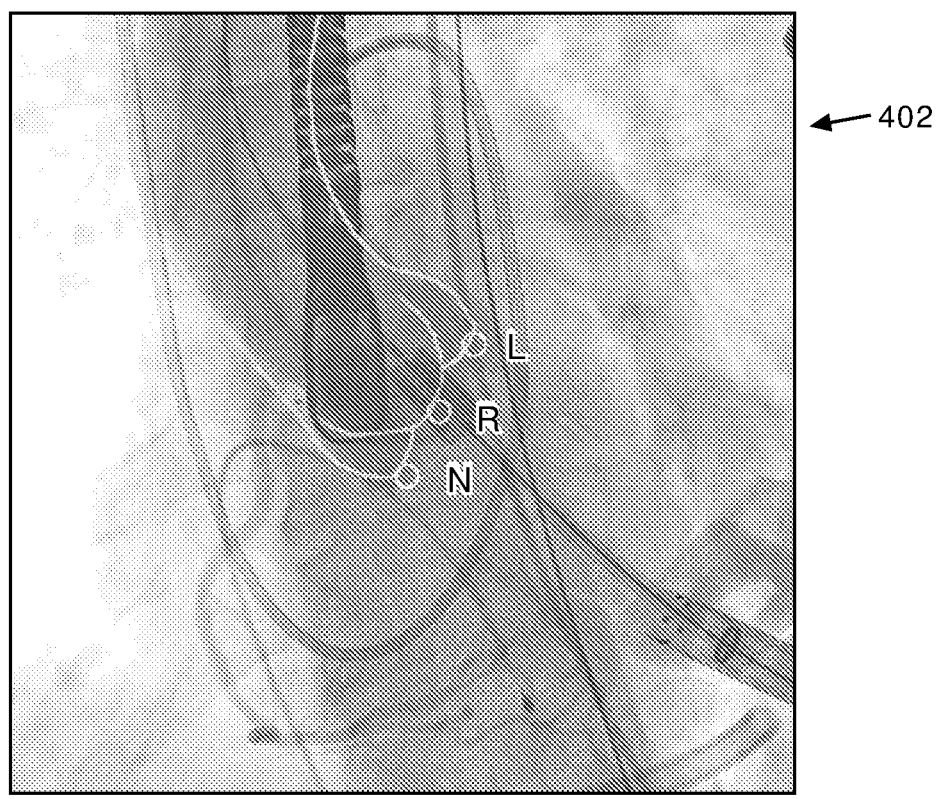
FIG. 4 is an image of an improved co-planar view showing a perspective of three valve cusp nadirs of an aortic valve aligned and equidistant from each other in accordance with one embodiment.

Referring to FIG. 4, an improved co-planar view is computed by the processor 114 to provide a perspective that shows three valve cusp nadirs (right (R), non (N) and left (L)) of the native aortic valve aligned and equidistant from each other as depicted in image 402. Other improved views may also be computed. For example, for a Medtronic™ CoreValve™ device, the view optimization attempts to find a view such that the non-coronary cusp is as inferior as possible, but on a line with the other two cusp nadirs. As more TAVR devices become available on the market, improved view parameters for these specific devices can also be configured within the workstation 112.

While the aortic valve is described, the present principles are applicable for procedures involving other anatomical features including all heart valves (four), and other prosthesis implants. For example, in one embodiment, the prosthesis (102) may include a mitral clip and the reference positions include both commissures and cusps of a mitral valve and a mitral valve annulus. The commissures, cusps and the mitral valve annulus may be indicated on a native mitral valve in the images 136 of the real-time imaging system 110. The selected improved view parameters may include a spatial relationship between the commissures, cusps and mitral valve annulus of the native mitral valve.

Referring to FIG. 5, an optimized cardiac ultrasound image 504 is derived from a full volume in image 502 based on the geometric information which can originate from either features in the ultrasound or the positioning of the device. In this case, the optimized view 504 shows the septum (Septum) with left (LA) and right atrium (RA) as well as the position of a TEE probe (OSS TEE) and guide wire (GW), both of which are enabled with FORS™.

Figure 6:
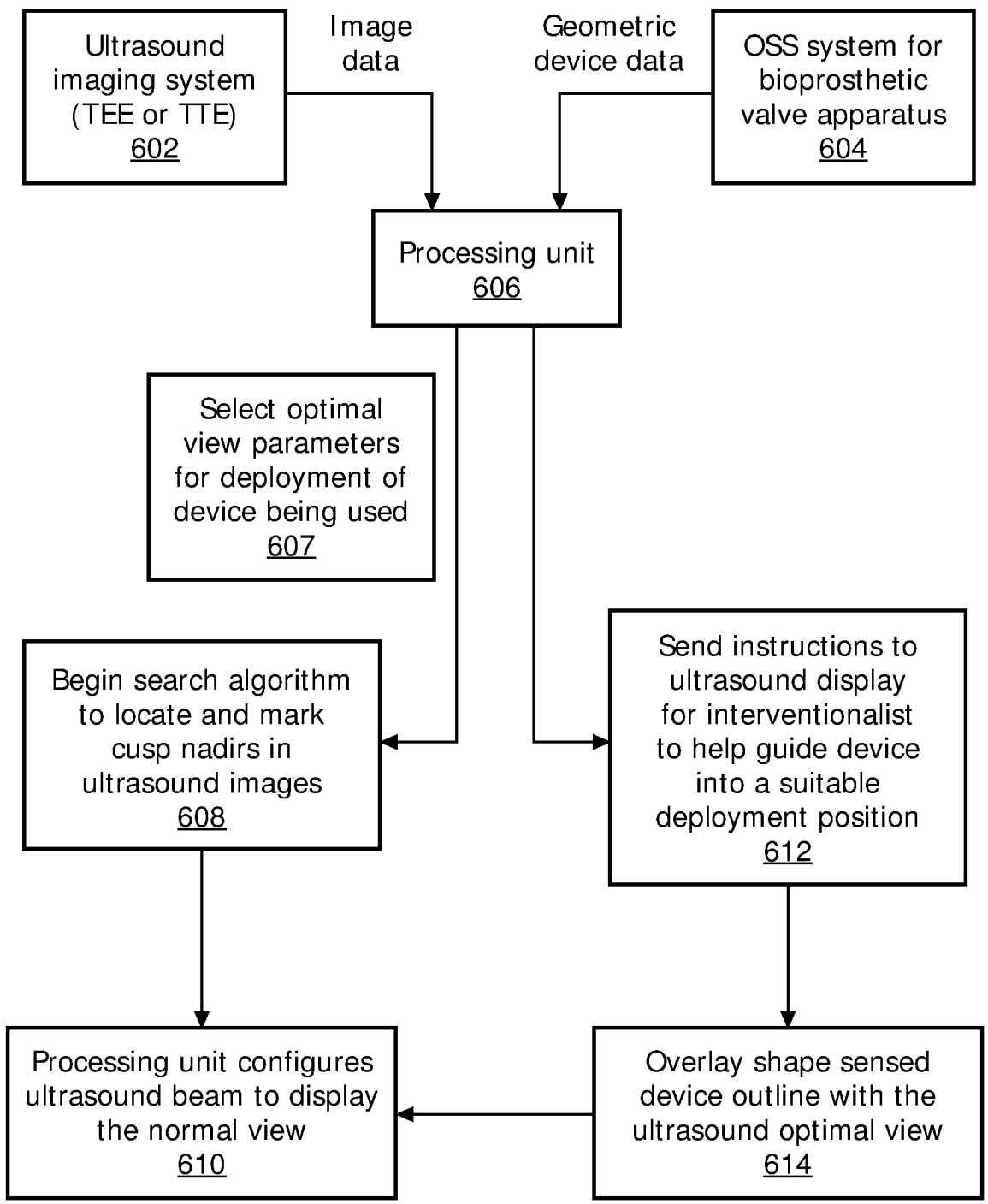
FIG. 6 is a block/flow diagram showing a system/method for determining and implementing an improved view in a transcatheter aortic valve replacement procedure using a combined FORS™/ultrasound image guidance system in accordance with one embodiment.

Referring to FIG. 6, a block/flow diagram shows a system/method 600 for determining and implementing an improved view in TAVR using a combined FORS™/ultrasound image guidance system. System 600 may be implemented as system 100 (FIG. 1); however, system 600 is directed at prosthetic implants as will be described. In block 602, ultrasound imaging is performed concurrently with positioning of a bioprosthetic valve. The imaging data is provided to a processing unit 606 (e.g., workstation 112). In block 604, real-time geometric data of the shape-sensed bioprosthetic valve position and orientation will be sent back to a processing unit 606. These data will be used by the processing unit 606 to calculate, send and display a simple set of instructions to the interventionalist as to how the device can be steered and positioned properly in the native aortic annulus within the improved view before deployment in block 612. The improved view parameters are selected based on the patient anatomy, the type of bioprosthetic device and user preferences, for example, positioning of cusp nadirs, etc. In block 608, a search program is initiated to locate the improved view parameters in the anatomy, e.g., locate and mark cusp nadirs in the ultrasound images. The shape-sensed display of the device can be overlaid with the improved view image from the ultrasound system in block 614. In block 610, the processing unit configures the ultrasound beam to display the improved view.

In block 608, a 2D x-ray aortogram may be employed as an initialization step to locate the approximate a region of all, e.g., three native aortic valve cusps. Assuming that the x-ray and ultrasound systems are registered, these data could then be sent to the processing unit 606 as a starting point for the search program (140, FIG. 1) to locate the cusp nadirs in the ultrasound images. This x-ray initialization could be used as either an alternative or a complement to an ultrasound based model of the aortic anatomy to initialize the search program.

In one embodiment, the processing unit 606 may be configured to track the markers on the native valve cusp nadirs such that the markers move with the cusps in the images. This information could then be employed to update and maintain the improved view and beam configuration from the ultrasound system in real-time with cardiac motion. Concurrently, the instructions to position the device for deployment could be displayed and optimized in such a way to account for this cardiac motion in block 612.

In block 607, the processing unit 606 may output a series of visualizations, and the operator may select a preferred view. This view is then marked as the improved view and shown to the clinicians. The improved view could be patient-specific, disease specific, or clinician/site specific and be stored in a database or memory (116, FIG. 1). Examples of improved views for TAVR may include, e.g., one or more of: 2D ultrasound slice showing the coronary or non-coronary cusps and the device with respect to the cusps; a bi-plane view showing the cusps and the deployment device; a bi-plane view showing the cusps and where the device should be with respect to the cusps; 3D ultrasound showing the cusps and device; multiple views of the cusps and device in different orientations shown next to each other; etc.

In other embodiments, the system 600 may include device positioning and deployment of other components, e.g., mitral clip procedures where a clip is fastened to leaflets of the mitral valve to reduce mitral regurgitation. Several ultrasound views are needed to guide these procedures, including a 3D TEE en face mitral valve view and a 2D TEE x-plane view of the mitral valve. Based on the visibility requirements of the native mitral valve leaflets and commissures in ultrasound images, improved view parameters to position and deploy mitral clips could be implemented into the processing unit 606. In other embodiments, the integration of an intracardiac echocardiography (ICE) catheter may be employed using system 600. This system 600 would be a more compact alternative to TEE or TTE based imaging. The processing unit 606 in this case would deliver instructions to the interventionalist to guide and manipulate the ICE catheter in such a way as to generate an improved view for the procedure in block 612.

In another embodiment, the instructions in block 612 from the processing unit 606 may be sent to a robotic platform (150, FIG. 1) to automatically manipulate either the ultrasound probe or the shape-sensed device to generate the improved view, and to position the device correctly in the improved view before deployment. This automated platform could be further enhanced with controls for the interventionalist or echocardiographer if additional manual manipulation is needed.

The applications in accordance with the present principles improve image guidance and workflow for both the echocardiographer and interventionalist when performing, e.g., TAVR or other procedures. The present principles improve patient safety as well, by reducing the amount of x-ray ionizing radiation and contrast agent needed to complete a TAVR procedure.

Figure 7:
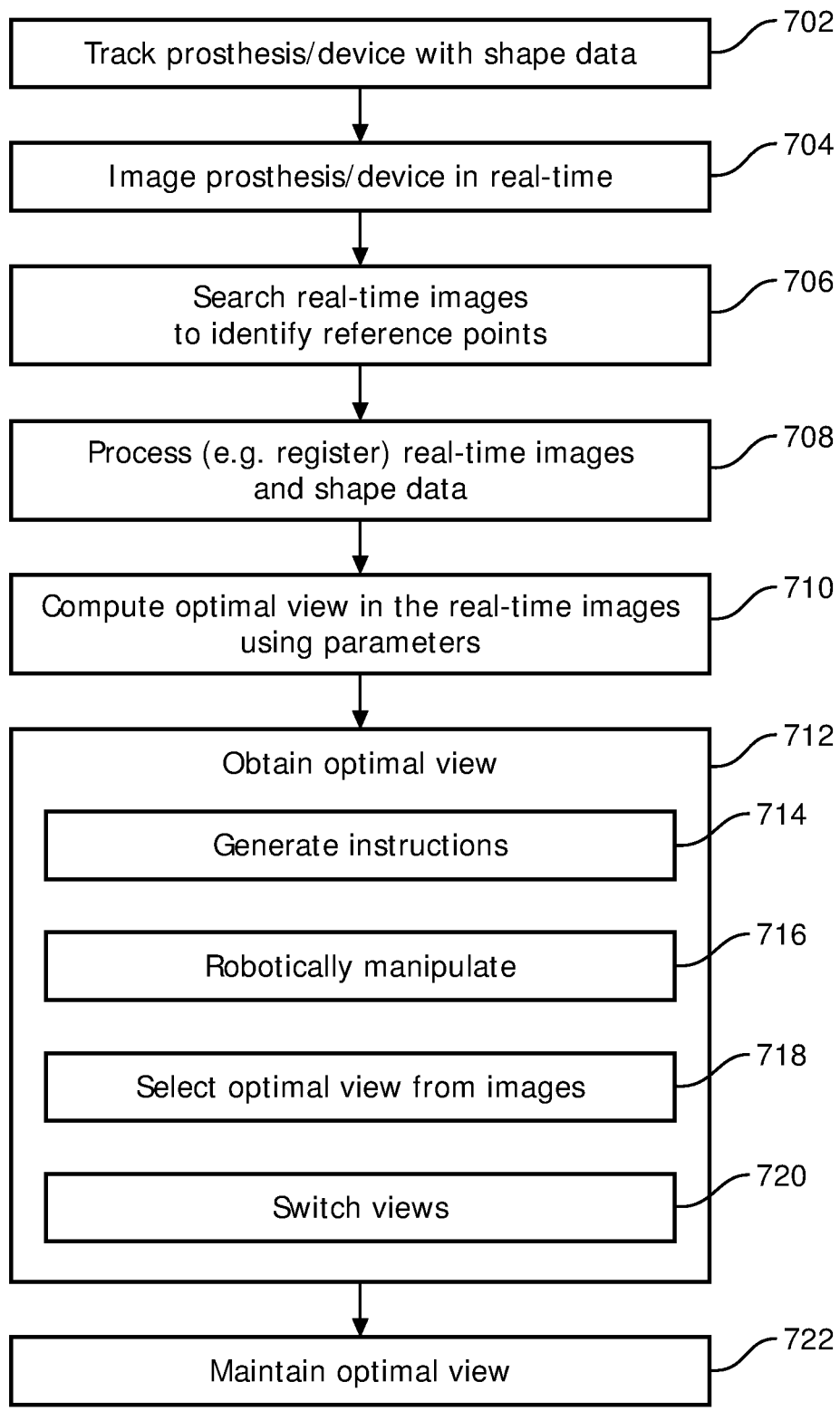
FIG. 7 is a flow diagram showing a method for finding improved views in accordance with illustrative embodiments.

Referring to FIG. 7, methods for finding improved views in prosthetic implant procedures are illustratively depicted. In block 702, a prosthesis is tracked in a volume using a shape sensing optical fiber system (FORS™) to generate shape data. The shape sensing fibers are disposed on the prosthesis or other device (deployment or guidance device) to ensure knowledge of the position and location of reference points or features on the prosthesis or device. In one example, the prosthesis includes an aortic valve with the reference positions including a left coronary cusp (LCC), right coronary cusp (RCC) and non-coronary cusp (NCC) indicated in the real-time images. Other devices may be employed.

In block 704, a real-time imaging system with a non-ionizing radiation source, such as ultrasound, is employed to image the volume having the native valve (e.g., aortic, mitral, etc.) and the prosthesis. In block 706, the real-time images are searched to identify reference positions of the native valve in the volume. In block 708, the real-time images and the shape data are processed to overlay the real-time images and the shape data in a same image for display. The processing may include registering the real-time images with a visual depiction of the shape data. In block 710, an improved view is computed in accordance with improved view parameters. The improved view parameters may include a view that depicts reference points or features in a certain way, e.g., as far apart as possible, equidistant from each other, a particular feature on the bottom, or other geometric relationship. The improved view parameters may include showing the prosthesis or device in a user-preferred or user-selected view. In the example above, the improved view parameters may include a spatial relationship between the LCC, RCC and NCC (e.g., equidistant from each other, etc.) or mitral valve features (e.g., cusps, annulus, etc.).

In block 712, the improved view is obtained for positioning the prosthesis. This may include redirecting the real-time imaging beam, moving an imaging probe, shifting the prosthesis/device, etc. In block 714, instructions are generated for obtaining the improved view. The instruction may be sent to the imaging device to change imaging configurations, may be rendered in speech or text for directing a user or may be sent to a robot to robotically manipulate at least one of the prosthesis or an imaging probe in accordance with the instructions in block 716. In block 718, images of the shape data and/or the real-time images may be displayed to permit a user to select an image as the improved view. Then, the improved view can be obtained. In block 720, the display may render multiple views and the system may switch between views. The improved views may include a view for a delivery device, e.g., a guide wire or catheter for delivering the prosthesis/device, a view for a native valve in the volume, a view for another anatomy of interest, etc. In block 722, the improvement is maintained. This may include accounting for patient movement, etc.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods to find improved views in transcatheter aortic valve replacement with combined optical shape sensing and ultrasound image guidance (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for finding a view of a volume having a prosthesis therein, comprising:

a shape sensing optical fiber system disposed on or in the prosthesis, wherein the shape sensing optical fiber system is configured to produce shape data of the prosthesis and to track the prosthesis in the volume;

a real-time imaging system comprising a non-ionizing radiation source, wherein the real-time imaging system is configured to create images of the volume having the prosthesis, and reference positions in the volume; and a memory comprising:

first instructions, which, when executed by a processor, causes the processor to search the images to identify the reference positions in the volume; and second instructions, which, when executed by the processor cause the processor to overlay an outline of a shape of the prosthesis from the shape data and the images, and to compute the view of the volume in accordance with view parameters specified for the prosthesis based on the identified reference positions in the volume.

2. The system as recited in claim 1, wherein the reference positions include a left coronary cusp (LCC), a right coronary cusp (RCC) and a non-coronary cusp (NCC), wherein the reference positions are indicated on a native aortic valve in the images of the volume.

3. The system as recited in claim 2, wherein the view parameters include a spatial relationship among the LCC, the RCC and the NCC on the native aortic valve and a deployment device for the prosthesis or any combination thereof.

4. The system as recited in claim 1, wherein: the prosthesis comprises a mitral clip: and the reference positions include commissures and cusps of a mitral valve and a mitral valve annulus, wherein the reference positions are indicated on a native mitral valve in the images of the volume.

5. The system as recited in claim 4, wherein the view parameters include a spatial relationship among the commissures, the cusps and the mitral valve annulus on the native mitral valve.

6. A system for finding a view of a volume having a prosthesis therein, comprising:

a shape sensing optical fiber system disposed on or in the prosthesis configured to track the prosthesis in the volume, wherein the shape sensing optical fiber system is configured to generate shape data indicating a location and position of the prosthesis within the volume;

an ultrasonic imaging system, wherein the ultrasonic imaging system is configured to create real-time anatomical images of the volume having the prosthesis; and a memory comprising:

first instructions, which when executed by a processor, cause the processor to register the shape data with the real-time anatomical images;

second instructions, which when executed by the processor, cause the processor to search the real-time anatomical images to identify reference positions in the volume; and third instructions, which when executed by the processor cause the processor to overlay an outline of a shape from the registered shape data and the real-time anatomical images, and to compute the view in accordance with view parameters specified for the prosthesis based on the identified reference positions in the volume, wherein the processor is adapted to configure the ultrasonic imaging system to maintain the view.

7. The system as recited in claim 6, wherein the reference positions including a left coronary cusp (LCC), a right coronary cusp (RCC) and a non-coronary cusp (NCC), which are indicated in the real-time anatomical images on a native aortic valve.

8. The system as recited in claim 7, wherein the view parameters include a spatial relationship between the LCC, the RCC and the NCC on the native aortic valve.

9. The system as recited in claim 6, wherein: the prosthesis includes a mitral clip; and the reference positions include commissures and cusps of a mitral valve and a mitral valve annulus, wherein the reference positions are indicated on a native mitral valve in the real-time anatomical images.

10. The system as recited in claim 9, wherein the view parameters include a spatial relationship between the commissures, the cusps and the mitral valve annulus on the native mitral valve.

11. A method for finding a view, the method comprising:
tracking a prosthesis in a volume having the prosthesis using a shape sensing optical fiber system to generate shape data;
real-time imaging with a non-ionizing radiation source to image the volume having the prosthesis in the volume to create real-time images;
searching the real-time images to identify reference positions in the volume;
processing the real-time images and the shape data to overlay the real-time images and an outline of a shape of the prosthesis from the shape data;
computing the view in accordance with view parameters which are specified for the prosthesis, based on the identified reference positions in the volume; and
obtaining the view for positioning the prosthesis.

12. The method as recited in claim 11, wherein the reference positions include a left coronary cusp (LCC), a right coronary cusp (RCC) and a non-coronary cusp (NCC), which are indicated on a native aortic valve in the real-time images.

13. The method as recited in claim 12, wherein the view parameters include a spatial relationship between the LCC, the RCC and the NCC on the native aortic valve.

14. The method as recited in claim 11, wherein the prosthesis includes a mitral clip and wherein the reference positions include both commissures and cusps of a mitral valve and a mitral valve annulus, which are indicated on a native mitral valve in the real-time images.

15. The method as recited in claim 14, wherein the view parameters include a spatial relationship between the commissures, the cusps and the mitral valve annulus of the native mitral valve.

* * * * *